United States Patent [19]

Chatterjee

[11] Patent Number: 5,248,605
[45] Date of Patent: Sep. 28, 1993

[54] CLONING AND EXPRESSING RESTRICTION ENDONUCLEASES FROM HAEMOPHILUS

[75] Inventor: Deb K. Chatterjee, Potomac, Md.

[73] Assignee: Life Technologies, Inc., Gaithersburg, Md.

[21] Appl. No.: 986,551

[22] Filed: Dec. 7, 1992

[51] Int. Cl.⁵ ................. C12N 9/22; C12N 15/55
[52] U.S. Cl. ..................... 435/199; 435/252.33; 435/320.1; 435/193
[58] Field of Search ............. 435/199, 193, 252.33, 435/320.1

[56] References Cited

U.S. PATENT DOCUMENTS

| | | | |
|---|---|---|---|
| 4,983,542 | 1/1991 | Van Cott et al. | 435/172.3 |
| 4,996,151 | 2/1991 | Brooks et al. | 435/172.3 |
| 5,002,882 | 3/1991 | Lunnen et al. | 435/172.3 |
| 5,082,784 | 1/1992 | Chatterjee et al. | 435/252.3 |
| 5,147,800 | 9/1992 | Hammond et al. | 435/252.3 |
| 5,179,015 | 1/1993 | Wilson et al. | 435/172.3 |

FOREIGN PATENT DOCUMENTS 0193413 9/1986 European Pat. Off. .

OTHER PUBLICATIONS

Wilson, G. G., Organization of restriction-modification systems, *Nucleic Acids Research* 19(10):2539-2566 (1991).
Wilson, G. G., Type II restriction-modification systems, *TIG* 4(11):314-318 (1988).
Bartolomé et al., Construction and properties of a family of pACYC184-derived cloning vectors compatible with pBR322 and its derivatives, *Gene* 102:75-78 (1991).
Card et al., Cloning and characterization of the HpaII methylase gene, *Nucleic Acids Research* 18(6):1377-1383 (1990).
Darzins et al., Cloning of Genes Controlling Aliginate Biosynthesis from a Mucoid Cystic Fibrosis Isolate of *Pseudomonas aeruginosa*, *Journal of Bacteriology* 159(1):9-18 (1984).
Hammond et al., Cloning the KpnI restriction-modification system in *Escherichia coli*, *Gene* 97:97-102 (1991).
Janulaitis et al., Cloning of the modification methylase gene of *Bacillus centrosporus* in *Escherichia coli*, *Gene* 20:197-204 (1982).
Kiss et al., Molecular cloning and expression in *Escherichia coli* of two modification methylase genes of *Bacillus subtilis*, *Gene* 21:111-119 (1983).
Lunnen et al., Cloning type-II restriction and modification genes, *Gene* 74:25-32 (1988).
Mann et al., Cloning of Restriction and Modification Genes in *E. coli*: The HhaII System From *Haemophilus haemolyticus*, *Gene* 3:97-112 (1978).
Piekarowicz et al., A new method for the rapid identification of genes encoding restriction and modification enzymes, *Nucleic Acids Research* 19(8):1831-1835 (1991).
Roberts, R. J., Restriction enzymes and their isoschizomers, *Nucleic Acids Research* 17(Suppl):r347-r387 (1989).
Stratagene Catalog p. 103 (1989).
Szomolanyi et al., Cloning the modification methylase gene of *Bacillus sphaericus* R in *Escherichia coli*, *Gene* 10:219-225 (1980).
Van Cott et al., Cloning the FnuDI, NaeI, NcoI and XbaI restriction-modification systems, *Gene* 74:55-59 (1988).
Walder et al, Cloning of the MspI Modification Enzyme, The Site of Modification and Its Effects on Cleavage by MspI and HpaII, *The Journal of Biological Chemistry* 258(2):1235-1241 (1983).
Wilson, G. G., Cloned restriction-modification systems—a review, *Gene* 74:281-289 (1988).

*Primary Examiner*—Charles L. Patterson, Jr.
*Attorney, Agent, or Firm*—Sterne, Kessler, Goldstein & Fox

[57] ABSTRACT

The present invention is directed to recombinant hosts which contain and express the HpaII Type-II restriction endonuclease gene. The present invention is also directed to vectors or DNA molecules which contain this gene, and to methods of producing the enzyme. One source of this enzyme is *Haemophilus parainfluenzae*, although other microorganisms may be used to isolate the restriction endonuclease isoschizomers of the invention.

19 Claims, 1 Drawing Sheet

CLONING AND EXPRESSING RESTRICTION ENDONUCLEASES FROM HAEMOPHILUS

FIELD OF THE INVENTION

This invention is directed to recombinant hosts expressing restriction endonucleases from the genus Haemophilus. This invention is specifically directed to the recombinant hosts and vectors which contain the gene coding for the restriction endonuclease HpaII. This invention is also directed to the cloned restriction endonucleases and their isoschizomers.

BACKGROUND OF THE INVENTION

Restriction endonucleases are in a class of enzymes that occurs naturally in prokaryotic and eukaryotic organisms. When restriction endonucleases are purified away from other contaminating cellular components, the enzymes can be used in the laboratory to cleave DNA molecules in a specific and predictable manner. Thus, restriction endonucleases have proved to be indispensable tools in modern genetic research.

Restriction endonucleases cleave DNA by recognizing and binding to particular sequences of nucleotides (the "recognition sequence") along the DNA molecule. The enzymes cleave both strands of the DNA molecule within, or to one side of, this recognition sequence.

Different restriction endonucleases have affinity for different recognition sequences. About 100 kinds of different endonucleases have so far been isolated from many microorganisms, each being identified by the specific base sequence it recognizes and by the cleavage pattern it exhibits. In addition, a number of restriction endonucleases, called restriction endonucleases isoschizomers, have been isolated from different microorganisms which in fact recognize the same recognition sequence as those restriction endonucleases that have previously been identified. These isoschizomers, however, may or may not cleave the same phosphodiester bond as the previously identified endonuclease.

Modification methylases are complementary to their corresponding restriction endonucleases in that they recognize and bind to the same recognition sequence. However, in contrast to restriction endonucleases, methylases chemically modify certain nucleotides within the recognition sequence by the addition of a methyl group. Following this methylation, the recognition sequence is no longer bound or cleaved by the restriction endonuclease. Thus, in nature, methylases serve a protective function, i.e., to protect the DNA of an organism which produces its corresponding restriction enzyme.

Restriction enzymes and modification methylases can be purified from the host organism by growing large amounts of cells, lysing the cell walls, and purifying the specific enzyme away from the other host proteins by extensive column chromatography. However, the amount of restriction enzyme relative to that of the other host proteins is usually quite small. Thus, the purificatio of large quantities of restriction enzymes or methylases by this method is labor intensive, inefficient, and uneconomical. By cloning the genes encoding for the desired restriction and modification enzymes and overexpressing them in a well studied organism, such as *Escherichia coli* (*E. coli*), the amount of these enzymes, relative to that of the host proteins, may be increased substantially.

SUMMARY OF THE INVENTION

The present invention is directed to recombinant hosts which contain and express the Type-II restriction endonuclease gene of the present invention. The restriction enzyme of the invention recognizes the palindromic sequence:

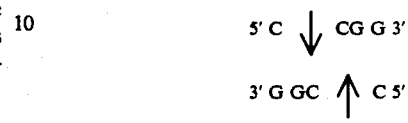

and cleaves the sequence between the two deoxycytidine (C) residues from the 5' end, producing a two-base 5' extension. This invention is further directed to a process for obtaining this enzyme and the use thereof.

In particular, the present invention is concerned with genes coding for restriction endonuclease, HpaII.

DEFINITIONS

Figure 1:
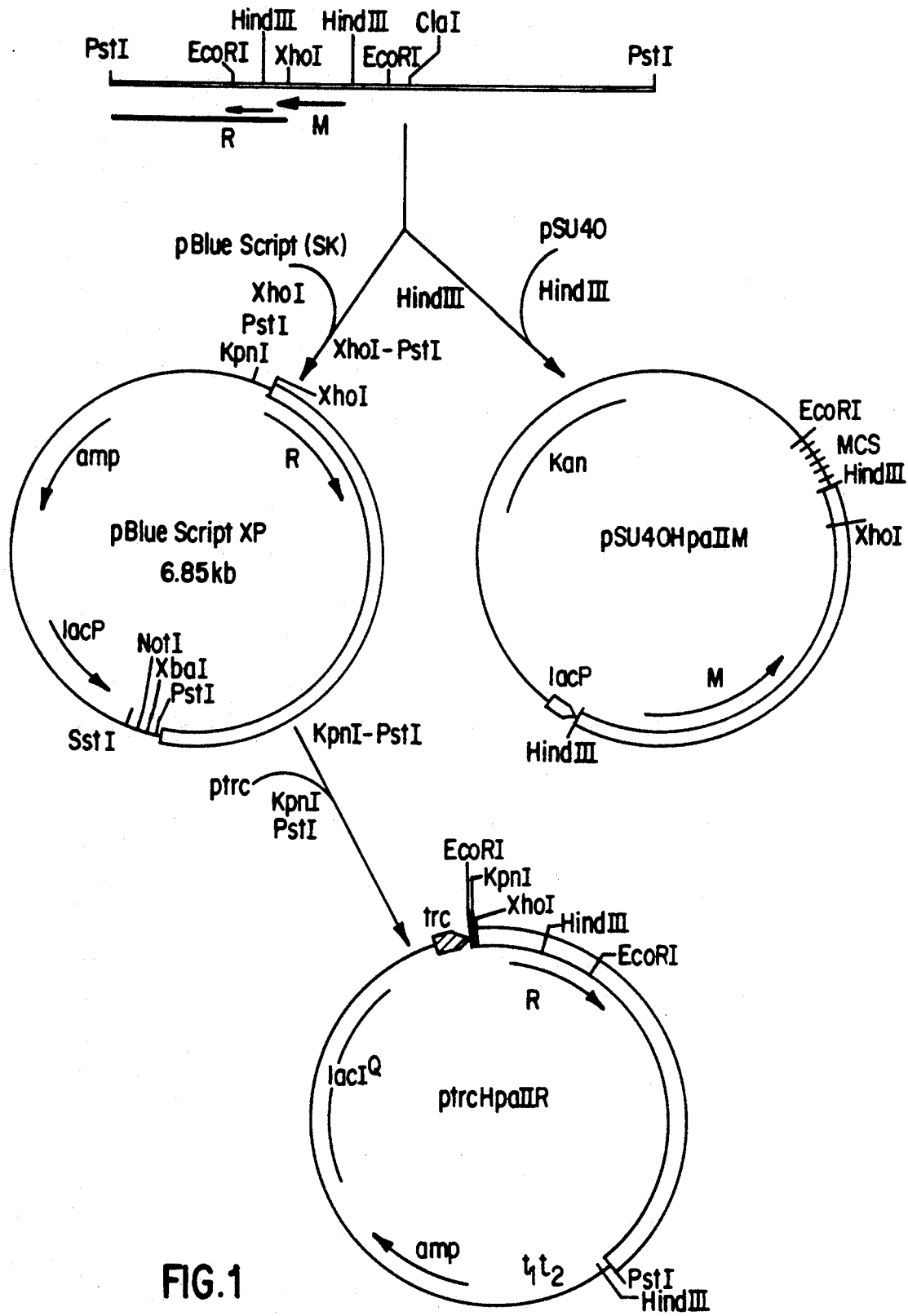
FIG. 1 shows a partial restriction map of a 12 kilobase (kb) PstI fragment and indicates the relative positions of the HpaII restriction endonuclease (R) and methylase (M) genes, as well as the strategy for cloning these genes. The figure also shows restriction maps of the plasmids ptrcHpaIIR and pSU40HpaIIM which contain and express the genes encoding HpaII and HpaII methylase (M.HpaII), respectively.

In the description that follows, a number of terms used in recombinant DNA (rDNA) technology are extensively utilized. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences.

Substantially pure. As used herein means that the desired purified enzyme is essentially free from contaminating cellular components, said components being associated with the desired enzyme in nature. Contaminating cellular components may include, but are not limited to, phosphatases, exonucleases or other undesirable endonucleases.

Restriction endonuclease isoschizomer. A restriction endonuclease isoschizomer is a term used to designate a group of restriction endonucleases that recognize and bind to the same recognition sequence but are isolated from different microbial sources. Restriction endonuclease isoschizomers may or may not cleave in the exact location as the restriction endonuclease with which it is being compared.

Modification methylase isoschizomer. A modification methylase isoschizomer is a term used to designate a group of modification methylases that recognize the same recognition sequence but are isolated from different microbial sources. Modification methylase isoschizomers may or may not chemically modify the same nucleotides within the recognition sequence as the restriction endonuclease with which it is being compared.

Recognition sequence. Recognition sequences are particular sequences which restriction endonucleases and modification methylases recognize and bind along the DNA molecule. Recognition sequences are typically four to six (and in some cases, eight) nucleotides in length with a two-fold axis of symmetry.

Recombinant Host. Any prokaryotic or eukaryotic microorganism which contains the desired cloned genes on an expression vector or cloning vector. This term is also meant to include those microorganisms that have been genetically engineered to contain the desired gene(s) in the chromosome or genome of that organism. The term "recombinant host" is not meant to include the wild type Haemophilus strain which produces HpaII.

Recombinant vector. Any cloning vector or expression vector which contains the desired cloned gene(s).

Host. Any prokaryotic or eukaryotic microorganism that is the recipient of a replicable expression vector or cloning vector. A "host," as the term is used herein, also includes prokaryotic or eukaryotic microorganisms that can be genetically engineered by well known techniques to contain desired gene(s) on its chromosome or genome.

Promoter. A DNA sequence generally described as the 5' region of a gene, located proximal to the start codon. The transcription of an adjacent gene(s) is initiated at the promoter region.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a structural gene produces a polypeptide. It involves transcription of the gene into mRNA and the translation of such mRNA into polypeptide(s).

Nomenclature for naming restriction endonucleases are in accord with the proposal of Smith et al., *J. Mol. Biol.* 81:419–423 (1973). Briefly, the first letter "H" of HpaII designates the genus "Haemophilus" while the lower case letters "pa" designate the species "parainfluenzae." Thus, the original strain found to produce HpaI and HpaII was designated *Haemophilus parainfluenzae* (American Type Culture Collection catalog number ATCC 49669; originally provided by Dr. Jane Setlow).

DETAILED DESCRIPTION OF THE INVENTION

The invention is directed to recombinant hosts which express the gene encoding for the Type-II restriction endonuclease HpaII and to DNA molecules which contain the gene. HpaII recognizes the palindromic sequence 5' CCGG 3', cleaving between the two C residues from the 5' end, producing a two-base 5' extension. The double-stranded recognition site of HpaII is thus characterized as follows:

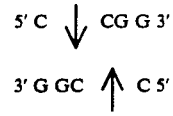

(wherein G represents deoxyguanosine and C represents deoxycytidine).

Also provided in this invention are recombinant hosts and DNA molecules which contain genes encoding for isoschizomers of the restriction endonuclease of the present invention (HpaII). Methods for producing the enzymes of the invention are also disclosed.

I. Isolation of the Genes Encoding Restriction Endonuclease and Modification Methylase or Isoschizomers thereof The restriction endonuclease and its corresponding modification methylase (HpaII and M.HpaII) may be obtained from any strain of H. parainfluenzae. Genes encoding isoschizomers of these enzymes can be obtained from any genus including, but not limited to, Arthrobacter, Bacillus, Citrobacter, Enterobacter, Escherichia, Flavobacterium, Haemophilus, Klebsiella, Micrococcus, Xanthomonas, Nocarida, Pseudomonas, Salmonella, and Streptomyces. The preferred genus to isolate isoschizomers of the restriction endonuclease of the present invention is Haemophilus.

Any strain of Haemophilus capable of producing restriction endonuclease isoschizomers of HpaII can be used for the purpose of this invention. For example, *Haemophilus aegyptus, Haemophilus gallinarum, Haemophilus haemolyticus, Haemophilus influenzae, Haemophilus parainfluenzae,* and *Haemophilus parahaemolyticus* may be used to obtain the genes expressing the restriction endonuclease isoschizomers of HpaII.

The preferred species for obtaining the gene encoding the enzyme of the present invention is *Haemophilus parainfluenzae* as described in the examples.

II. Cloning and Expressing the Genes Encoding for the Restriction Endonuclease and Modification Methylase or Isoschizomers thereof HpaII and M.HpaII are preferably obtained by isolating the genes encoding for the enzymes from *Haemophilus parainfluenzae* and then cloning and expressing them. It is understood in this invention that genes coding for isoschizomers of the restriction endonucleases and modification methylases of the present invention may be obtained from any microorganism including the genus Haemophilus by using the recombinant techniques described herein.

DNA molecules which code for HpaII and M.HpaII, or isoschizomers thereof, can be recombined into a cloning vector and introduced into a host cell to enable the expression of the restriction endonuclease or modification methylase by that cell. DNA molecules may be recombined with vector DNA in accordance with conventional techniques, including restriction digestion to provide appropriate termini, filling in of cohesive ends as appropriate, alkaline phosphatase treatment to avoid undesirable joining, and ligation with appropriate ligases.

a. Hosts for Cloning and Expressing

The present invention encompasses the expression of the desired restriction endonuclease in prokaryotic and eukaryotic cells. Eukaryotic and prokaryotic hosts that may be used for cloning and expressing the enzyme of the invention are well known in the art. Vectors which replicate in such host cells are also well known (Maniatis et al., *Molecular Cloning: A Laboratory Manual*, Cold Spring Harbor Laboratory Press, Cold Spring Harbor, N.Y. (1982)).

Preferred prokaryotic hosts include, but are not limited to, bacteria of the genus Escherichia, Bacillus, Streptomyces, Pseudomonas, Salmonella, Serratia, Haemophilus, etc. The most preferred prokaryotic host us E. coli. Bacterial hosts of particular interest in the present invention include E. coli K12, DH10B (F$^-$, araD139 $\Delta$ (ara, leu) 7697, $\Delta$lacX74, galU, galK, mcrA, $\Delta$(mrr hsd RMS mcrB), rpsL dor, $\phi$80 d lacZ $\Delta$M15, endA1, nupG, recA1).

It has been found that *E. coli* has several mechanisms (restriction systems) for identifying foreign DNA and destroying it. This can be a significant problem in cloning experiments, resulting in reduced recovery of the desired sequences. In particular, it has been found that *E. coli* contains restriction systems that degrade DNA when it is methylated, either on cytosine residues or adenine residues. Specifically, the well known methylcytosine-specific systems include mcrA (rglA), and mcrB (rglB). The methyladenine-specific restriction system has been designated mrr. Thus, the preferred host for cloning and expressing the genes encoding for the enzymes of the present invention are hosts in which these types of restriction systems have been inactivated through mutation or loss.

b. Methods for Cloning and Expressing

HpaII and M.HpaII or isoschizomers thereof are preferably obtained by isolating the genes coding for the enzymes and then cloning and expressing them. Four different techniques for isolating and cloning restriction endonuclease and modification methylase have been described in a recent review by Wilson, *Gene* 74:281-289 (1988). The four methods reviewed include (1) subcloning of natural plasmids; (2) selection based on phage restriction; (3) selection based on vector modification involving methylation protection; and (4) multistep isolation.

The preferred method according to this invention is the vector modification technique, i.e., methylation protection. Methylation protection involves digestion of a plasmid library with the restriction enzyme to be cloned so that only plasmids whose sequences are modified, because of the presence of the methylase, will produce transformants in a suitable host. This selection has worked for cloning endonuclease and methylase genes together as well as methylase genes alone (Szomolanyi et al., *Gene* 10:219-225 (1980); Janulaitis et al., *Gene* 20:197-204 (1982); Kiss and Baldanf, *Gene* 21:111-119 (1983); Wilson, supra; and Wilson, *Nucleic Acids Res.* 19:2539-2561 (1991)).

The methylation protection method for cloning restriction endonuclease genes relies on the proximity of the methylase and restriction enzyme genes to each other and on the expression of both genes in the host cell such as *E. coli*. First, a library is constructed by ligating fragmented genomic DNA from the source organism into a vector. For this library, one chooses a vector having one or, preferably, more recognition sites of the restriction enzyme one wishes to clone. Preferably, vector pCP13 is used to construct the plasmid library (Darzins, A. et al., *J. Bacteriol.* 159:9-18 (1984)). Generally, library inserts are prepared by only partially digesting the genomic DNA in order to obtain a portion of DNA fragments which contain the intact gene of interest. Second, this library is transformed into and grown in a suitable host such as *E. coli*. Vector DNA that is subsequently isolated from these transformed and grown cells is called the plasmid library. The plasmid library is a mixture of different DNA molecules, having virtually all possible inserts and thus, is representative of most, if not all, DNA sequences contained in the source organism. The vector/insert combinations having a methylase gene will have methylated the recognition sequences within the vector/insert DNA and the host chromosomal DNA if the methylase is expressed in the host used, preferably, *E. coli*.

The isolated plasmid library DNA is then digested with the restriction enzyme. Unmethylated vector/insert combinations are degraded and methylated combinations surfive the endonuclease treatment. The endonuclease-treated DNA is then transformed into a fresh host cell. Degraded vector/insert combinations do not become established. Methylprotected vector/insert combinations, which survived the endonuclease treatment, can establish and maintain themselves in the new *E. coli* host cells, thereby forming clones.

Cell extracts of these clones are then assayed for restriction endonuclease activity in order to identify clones which express the desired restriction enzyme. Thus, genes for a methylase-restriction system can be cloned on a single recombinant DNA molecule, provided that the restriction endonuclease gene is closely linked to the methylase gene.

There are a number of reasons why the above method might not work with a particular endonuclease-methylase system. (1) The two genes (methylase and endonuclease) may not be closely linked. In that case, both genes cannot be on the same DNA fragment insert. (2) The cloned fragment may, by chance, contain only the methylase gene. For example, a closely linked endonuclease gene might be inactivated by being cut by the restriction enzyme that generated the DNA library. Similarly, the methylase and endonuclease genes may have been separated from each other by a cut at an intervening restriction site. (3) The level of expression of the endonuclease may be high relative to the expression level of the methylase. In this situation, before the expressed methylase can protect the host DNA, the expressed endonuclease destroys the vector/insert combination as well as degrades the chromosome(s) and may kill the host cell. Alternatively, deletion(s) resulting in loss of part or all of the endonuclease gene from the vector/insert combination may allow the host to survive. (4) The methylase gene may not be expressed in the new host, leading to lack of protection of DNA from the endonuclease. (5) The endonuclease gene may not be expressed in the new host. In situations (1) and (3), if the endonuclease is expressed in the host, there will be no methylase enzyme activity to protect DNA in the host cell and the attempt to clone the endonuclease would fail.

Card et al., *Nucleic Acids Res.* 18:1377-1383 (1990), have attempted the cloning of HpaII restriction and methylase enzymes. Although the HpaII methylase gene was successfully cloned in several DNA fragments which were large enough to contain the genes for both enzymes, the restriction enzyme activity was not detected and the gene encoding the endonuclease was not identified in these clones.

In the present invention, the HpaII methylase gene was cloned in a cosmid vector using the methylase protection technique. However, the initial clones did not produce detectable restriction enzyme activity. Since most of the Type-II restriction-modification systems are closely linked, the clones which contained large DNA fragments should have contained the genes for both enzymes. Thus, it was possible that the HpaII restriction enzyme gene is expressed at a relatively low level and as a result, the clones did not display any detectable restriction enzyme activity.

In order to find the possible open-reading frame for the restriction enzyme, cloned DNA was sequenced at the 3' end of the methylase gene and the adjacent region. The cloned sequence differs from the published sequence of Card et al., supra, by two bases. By correcting these two bases, a potential open-reading frame was identified which was absent from the published sequence.

To separate the putative restriction enzyme gene from the methylase gene, a 3.9 kb DNA fragment containing the 3' end of the methylase gene and adjacent DNA sequences was subcloned into a vector and placed under the control of a strong promoter. The subcloning was performed in such a way that the strong promoter was placed in tandem with the newly-discovered open-reading frame. The clone was then introduced into a host expressing HpaII methylase in a compatible plasmid. The recombinant DNA hosts produced detectable HpaII activity. Thus, the precise identification of DNA fragments containing the restriction endonuclease gene required additional sequencing and subcloning of smaller DNA fragments into expression vectors.

Although the steps outlined above are the preferred mode for practicing the present invention, it will be apparent to those skilled in the art that the above-described approach can vary in accordance with techniques known in the art. For example, once the HpaII methylase and/or restriction genes are cloned based on the information disclosed herein, these gene sequences or synthetic oligonucleotides of these sequences may be used in hybridization experiments to obtain clones which contain these genes. See Maniatis et al., supra. Furthermore, one of ordinary skill in the art, using standard hybridization techniques, can utilize these sequences to isolate genes which encode for isoschizomers of the HpaII restriction and modification enzymes by altering the hybridization stringencies.

c. Methods for Enhancing Expression

Once the desired restriction endonuclease gene has been isolated, a number of recombinant DNA strategies exist for enhanced production of the desired protein in eukaryotic or prokaryotic hosts. These strategies, which will be appreciated by those skilled in the art, utilize high copy number cloning vectors, expression vectors, inducible high copy number vectors, etc.

Enhanced production of the restriction endonuclease can be accomplished, for example, by operably linking the desired gene to a strong prokaryotic promoter, although the natural restriction gene promoter may be used. Such well known promoters may be either constitutive or inducible. Examples of constitutive promoters include the int promoter of bacteriophage λ, and the bla promoter of the β-lactamase gene of pBR322, etc. Examples of inducible prokaryotic promoters include the major left and right promoters of bacteriophage λ ($P_L$ and $P_R$), the trp, recA, lacZ, gal, trc, and tac promoters of E. coli, the α-amylase (Ulmanen, I., et al., J. Bacteriol. 162:176–182 (1985)), the §-28-specific promoters of B. subtilis (Gilman, M. Z., et al., Gene 32:11-20 (1984)), the promoters of the bacteriophages of Bacillus (Gryczan, T. J., In: The Molecular Biology of the Bacilli, Academic Press, Inc., N.Y. (1982)), and Streptomyces promoters (Ward, J. M., et al., Mol. Gen. Genet. 203:468–478 (1986)). Prokaryotic promoters are reviewed by Glick, B. R., (J. Ind. Microbiol. 1:277–282 (1987)); Cenatiempo, Y. (Biochimie 68:506–516 (1986)); and Gottesman, S. (Ann. Rev. Genet. 18:415–442 (1984)).

In order to enhance the production of the desired restriction endonuclease in a prokaryotic cell, it is important to maintain expression of the corresponding modification methylase gene sufficient to protect the DNA of the recombinant host against cleavage with the cloned restriction endonuclease. Therefore, it may be necessary to enhance the level of methylase expression in conjunction with increased endonuclease activity.

Furthermore, those skilled in the art will recognize that both the restriction endonuclease and modification methylase genes need not be maintained on the same cloning or expression vector within the same recombinant host. The endonuclease gene, for example, may be located on one vector, while its corresponding methylase gene may be located on a separate vector or located on the host genome. Various combinations of maintaining both the modification and restriction genes within the same recombinant host can be constructed. The only requirement, when cloning restriction endonuclease genes, is that the recombinant host contain and express the methylase gene corresponding to the endonuclease gene being cloned.

III. Isolation and Purification of the Restriction Endonuclease from Recombinant Hosts The enzyme of this invention (HpaII) or an isoschizomer thereof is preferably produced by fermentation of the recombinant host (prokaryotic or eukaryotic) containing and expressing the cloned restriction endonuclease and modification methylase genes. The recombinant host, such as E. coli, producing the cloned proteins, can be grown and harvested according to techniques well known in the art.

After culturing, the recombinant host cells of this invention can be separated from the culture liquid, for example, by centrifugation. The restriction enzymes produced by this host can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, desired enzyme can be purified by extraction, ion-exchange chromatography, molecular-sieve chromatography, and the like, giving the restriction endonuclease of this invention.

According to the present invention, assays to detect the presence of the restriction endonucleases and modification methylases can be used during the conventional biochemical purification methods to determine the presence of these enzymes.

Restriction endonuclease can be identified on the basis of the cleavage of its recognition sequence. For example, lambda (λ) DNA can be used as a substrate. The DNA fragments obtained are separated electrophoretically in agarose gels in the buffer systems conventional for the fragment separation in the presence of ethidium bromide (EtdBr).

Demonstration of modification methylase activity can be, but is not limited to, a two-step identification process. First, substrate DNA (λDNA) that contains the recognition sequence is incubated with column fractions to be tested for methylase activity. Second, this DNA is then challenged with the corresponding restriction activity to identify those fractions which contain methylase activity. For example, while assaying for M.HpaII, the DNA samples will be challenged with HpaII. Thus, DNA samples which do not exhibit cleavage with HpaII contain M.HpaII activity.

The recombinant host containing the genes encoding for HpaII and M.HpaII (ptrcHpaIIR and pSU40HpaIIM in DH10B) was put on deposit with the Patent Culture Collection, Northern Regional Research Center, USDA, 1815 N. University Street, Peoria, Ill. 61604 USA (NRRL) as deposit No. NRRL B-21021 (deposit date Dec. 3, 1992).

Having now generally described the invention, the same will be more readily understood through reference to the following Examples which are provided by way of illustration, and are not intended to be limiting of the present invention, unless specified.

EXAMPLE 1

Bacterial Strains and Growth Conditions

E. coli strains were grown at 37° C. in Circle Grow (BIO 101, La Jolla, Calif.) or YET-maltose (yeast extract 1%, NaCl 0.5%, tryptone 0.5% and maltose 0.2%) with antibiotic supplements of ampicillin (Ap), 100 μg/ml; kanamycin (Kan), 50 μg/ml; or tetracycline (Tc), 20 μg/ml as required (unless indicated otherwise). E. coli DH10B competent cells or electrocompetent cells were obtained from Life Technologies, Inc. (LTI), Gaithersburg, Md. Haemophilus parainfluenzae, ATCC 49669, was obtained from the American Type Culture Collection, Rockville, Md.

EXAMPLE 2

DNA Isolation

Small scale plasmid DNA isolations were performed by an alkaline lysis method (Maniatis et al., *Molecular Cloning: A Laboratory Manual*, Cold Spring Harbor Laboratory, 1982). For large scale preparations, alkaline lysis was followed by standard CsCl-EtdBr gradient centrifugation (Maniatis et al., supra).

H. parainfluenzae total genomic DNA was isolated according to Marmur, *J. Mol. Biol.* 3:208–218 (1961).

EXAMPLE 3

Construction of Genomic Libraries

Genomic DNA of *Haemophilus parainfluenzae*, ATCC 49669, was digested partially with Sau3A1 as follows. Purified genomic DNA (50 μg) was digested in separate reactions with 5.0, 2.5, 1.25, 0.625, 0.312, 0.165, 0.0825, 0.0412, or 0.0205 units/μg DNA of Sau3A1 in 100 μl of 1×REact 4 (LTI). After the samples were incubated for 1 hour at 37° C., the DNA aliquots were analyzed by agarose gel electrophoresis. The remaining sample portions were kept at −70° C. in the presence of 10 mM EDTA.

Conditions required to achieve minimal digestion (90% of the DNA greater than 15 kb in length) were chosen as determined by gel electrophoresis. Sample number 3 was chosen to make a cosmid library.

Two micrograms of BamHI-cleaved pCP13 vector were ligated with 5 μg of the partially digested genomic DNA using one unit of T4 DNA ligase in 1×ligase buffer (LTI). The 30 μl ligation reaction was incubated at room temperature (25° C.) for 16 hours.

Approximately 1 to 1.5 μg of ligated DNA (5 μl of the ligation reaction mixture) was packaged using LTI's recommended procedure. After the packaging reaction was complete, *E. coli* cells were infected with the packaging mix as follows. DH10B cells were prepared by growing an overnight culture in YET medium containing 0.2% maltose. The next day, 500 μl of these cells were inoculated into 10 ml of YET medium containing 0.2% maltose and grown to midlog phase. These cells were then centrifuged and resuspended in 4.0 ml of sterile 10 mM MgSO$_4$ buffer. Two hundred microliters of the cell suspension were mixed with 100 μl of packaging mix. After a 30 minute incubation at 37° C. without shaking, a 700 μl volume of SOC medium (2% Bacto-tryptone, 0.5% Yeast extract, 10 mM NaCl, 2.5 mM KCl, 10 mM MgCl$_2$, 10 mM MgSO$_4$ and 20 mM glucose) was added. The cells were allowed to grow at 37° C. in an air shaker-incubator for 30 minutes. The cells were then placed onto YET agar plates containing tetracycline and incubated overnight.

Approximately $5 \times 10^3$ tetracycline-resistant colonies were obtained. The colonies were pooled by scraping the cells from the agar surface. This was accomplished by flooding each plate with 5 ml of filter-sterilized PEB I (50 mM glucose, 25 mM Tris-HCl pH 8.0 and 10 mM EDTA). After carefully resuspending the cells in buffer with a sterilized glass rod, the cell suspension was immediately inoculated into 500 ml of Circle Grow medium containing tetracycline.

After a 5 hour growth at 30° C., the cells were harvested. Plasmid DNA was isolated from this cell suspension according to Example 2. The isolated cosmid libraries were designated pCPHpaL.

EXAMPLE 4

Selection of Clones Expressing Methylase and Restriction Enzymes

Clones expressing the HpaII methylase were selected by digesting the cosmid library with an excess amount of HpaII. To select M.HpaII clones, 2 μg of pCPHpaL were digested in a reaction volume of 100 μl containing 1×REact 8 buffer (LTI) with 50 units of HpaII at 37° C. for 16 hours. The DNA was extracted with an equal volume of phenol:chloroform (1:1), ethanol precipitated, and dissolved in 10 μl of TE buffer.

*E. coli* DH10B competent cells were electroporated with 1 μl of the digested DNA library according to the manufacturer's suggested protocol. After electroporation, the cells were diluted with 900 μl of SOC medium and grown for 30 minutes at 37 ° C. One per cent, 10%, and 89% aliquots of the cell suspension were then plated on YET agar plates which contained tetracycline. The plates were incubated at 37° C. Approximately 600 tetracycline-resistant colonies were isolated after plating the cells.

Colonies that survived the methylase selection scheme were analyzed for the presence of methylase activity. Twelve clones that survived HpaII selection were individually inoculated and grown overnight in 2 ml of Circle Grow medium containing tetracycline. Small scale plasmid isolations were performed as previously described. The DNA preparations were then tested for their ability to resist cleavage with HpaII as follows.

A 0.5 to 1.0 μg amount of isolated DNA was digested in 1×REact 8 buffer with 10 units of HpaII at 37° C. for 1 hour in a 20 μl reaction. Protection of the resident plasmid and the host chromosomal DNA from digestion indicated the presence of methylase activity. Analysis of the plasmid DNA by agarose gel electrophoresis demonstrated that 10 out of the 12 clones were not cleaved with HpaII. The clones were saved and later assayed for restriction enzyme activity according to Example 5.

Although these clones apparently expressed methylase due to the resistance of plasmid DNA to HpaII digestion, the clones did not appear to have HpaII activity. Thus, additional steps were needed to determine the presence of the HpaII gene.

Plasmid DNA samples from the survivors of the methylase selection scheme were digested with restriction enzymes. Several clones contained a 2 kb HindIII fragment, a 3.3 kb EcoRI fragment, and a 12 kb PstI fragment. One of the clones, designated 3E, was chosen for further study. The plasmid DNA from this clone was digested with PstI and the 12 kb PstI fragment was cloned in pUC19 (LTI). The clone, designated pHpaII-1, was resistant to HpaII digestion, suggesting that the methylase is active. However, HpaII restriction enzyme activity was not detected.

FIG. 1 shows the partially mapped 12 kb PstI fragment. Cloning of a 1.2 kb XhoI-EcoRI fragment under the control of a strong promoter and in both orientations did not produce any restriction enzyme activity. Similarly, cloning of a 2.4 kb XhoI-ClaI fragment under the control of a strong promoter and in two different orientations did not produce any restriction enzyme activity. To determine whether the PstI fragment contains an open-reading frame for the restriction enzyme, the DNA fragment was sequenced from the XhoI site towards the 3' end of the methylase gene and continuing into the adjacent region.

The sequencing experiments revealed two interesting points. First, the DNA sequence adjacent to the methylase gene differed in two places compared with the sequence reported by Card et al. (supra). The DNA sequence of the PstI fragment contains an additional guanosine (G) between nucleotides 1754 and 1755 and an additional adenine (A) between nucleotides 1795 and 1796, compared with the published sequence. These two additional nucleotides provide an open-reading frame of 92 amino acids starting from nucleotide 1643 (ATG) and preceded by a ribosome-binding site (RBS) at 1632. There is, of course, another ATG in the same reading frame at nucleotide 1763 which is also preceded by a putative RBS. Thus, both sites in the PstI fragment have the potential to be the start site for HpaII restriction enzyme gene.

As shown in FIG. 1, the HpaII restriction endonuclease gene was isolated by subcloning the XhoI-PstI fragment in pBlueScript-SK (Stratagene; La Jolla, Calif.). The cloned fragment was then regenerated as a KpnI-PstI fragment and subcloned in ptrc99A (Pharmacia, Inc.; Piscataway, N.J.) at the KpnI-PstI sites. The resulting plasmid was designated ptrcHpaIIR. The plasmid, designated pSU40HpaIIM, was derived by cloning the 2 kb HindIII fragment containing the methylase gene in pSU40 (Bartolomé et al., *Gene* 102:75-78 (1991)). Recombinant hosts containing pSU40HpaIIM and ptrcHpaIIR were grown and assayed for HpaII activity with and without induction with isopropyl-β-D-thiogalactopyranoside (IPTG; 2 mM, final concentration). More than 50,000 units of HpaII were detected per gram of wet weight of cells after induction with IPTG.

EXAMPLE 5

Assay for Restriction Enzyme

Forty milliliters of YET medium with ampicillin and kanamycin were inoculated with 0.4 ml of overnight culture. The culture was grown at 30° C. to a density of 0.5 at $A_{590}$. A 20 ml aliquot was removed and induced with IPTG (2 mM, final concentration) for 2 hours at 30° C. The other 20 ml aliquot was saved as an uninduced culture and grown for 2 hours at 30° C. The cultures were centrifuged, and the cell pellets were resuspended in 0.9 ml of cold SB (10 mM Tris-HCl, pH 7.5, 10 mM β-mercaptoethanol, 1 mM EDTA). The cells were transferred to a 1.5 ml microcentrifuge tube and sonicated 3 times with 10 second bursts at a 100% duty cycle using a microtip probe. The cellular debris was removed by centrifuging 5 min at 14,000 g at 4° C. Phage lambda DNA (λ DNA) substrate was prepared in the 1×REact 8 buffer (LTI). Five microliters of the cell extract were serially diluted 3-fold through 3 more tubes. The reactions were incubated 30 minutes at 37° C. and analyzed on an agarose gel. Activity was determined by the presence of the appropriate size bands associated with a HpaII digest of λ DNA.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

All publications and patent applications mentioned in this specification are indicative of the level of skill of those in the art to which the invention pertains. All publications and patent applications are herein incorporated by reference to the same extent as if each individual publication or patent application was specifically and individually indicated to be incorporated by reference.

What is claimed is:

1. A recombinant host comprising a Haemophilus gene coding for a restriction endonuclease, said restriction endonuclease recognizing the palindromic sequence:

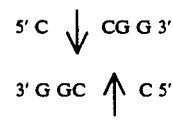

and cleaving said sequence between the two C residues, producing a two-base 5' extension.

2. The host of claim 1, wherein said gene is obtained from *Haemophilus parainfluenzae*.

3. The host of claim 2, wherein said gene is obtained from *Haemophilus parainfluenzae* ATCC 49669.

4. The host of claim 1, wherein said gene codes for HpaII.

5. A host of any one of claims 1 to 4, wherein said host is *E. coli*.

6. A vector comprising a Haemophilus gene coding for a restriction endonuclease, said restriction endonuclease recognizing the palindromic sequence:

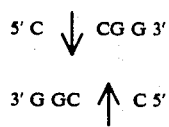

and cleaving said sequence between the two C residues, producing a two-base 5' extension.

7. The vector of claim 6, wherein said Haemophilus gene codes for HpaII.

8. The vector of any one of claims 6 or 7, wherein said endonuclease gene is under control of an inducible promoter.

9. The vector of claim 8, wherein said promoter is lambda $P_L$ promoter.

10. The vector of claim 8, wherein said promoter is a tac promoter.

11. A method of producing a restriction endonuclease which recognizes the palindromic sequence:

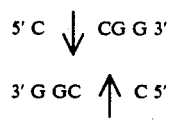

and cleaves said sequence between the two C residues, producing a two-base 5' extension, said method comprising:
(a) culturing a recombinant host comprising a Haemophilus gene coding for said restriction endonuclease; and
(b) isolating said restriction endonuclease from said host.

12. The method of claim 11, wherein said gene is obtained from *Haemophilus parainfluenzae*.

13. The method of claim 12, wherein said gene is obtained from *Haemophilus parainfluenzae* ATCC 49669.

14. The method of claim 11, wherein said gene codes for HpaII.

15. The method of any one of claims 11 to 14, wherein said host is *E. coli*.

16. The method of any one of claims 11 to 14, wherein said gene is contained by a vector.

17. The method of any one of claims 11 to 14, wherein said gene is under control of an inducible promoter.

18. The method of claim 17, wherein said promoter is a lambda $P_L$ promoter.

19. The method of claim 17, wherein said promoter is a tac promoter.

* * * * *